(12) United States Patent
Vilaplana Artigas et al.

(10) Patent No.: US 10,703,703 B2
(45) Date of Patent: *Jul. 7, 2020

(54) POLYMER DEGRADATION

(71) Applicant: Ioniqa Technologies B.V., Eindhoven (NL)

(72) Inventors: Marcel Vilaplana Artigas, Eindhoven (NL); Luuk Mestrom, Eindhoven (NL); Rick De Groot, Eindhoven (NL); Vincent Philippi, Eindhoven (NL); Carlos Guerreo Sanchez, Eindhoven (NL); Tonnis Hooghoudt, Eindhoven (NL)

(73) Assignee: Ioniqa Technologies B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/191,091

(22) Filed: Nov. 14, 2018

(65) Prior Publication Data

US 2019/0185406 A1    Jun. 20, 2019

Related U.S. Application Data

(63) Continuation of application No. 14/980,148, filed on Dec. 28, 2015, now Pat. No. 10,266,479, which is a continuation of application No. PCT/NL2014/050418, filed on Jun. 24, 2014.

(30) Foreign Application Priority Data

Jun. 24, 2013  (NL) .................................... 2011025

(51) Int. Cl.
| | | |
|---|---|---|
| *C07C 67/333* | (2006.01) | |
| *B01J 31/02* | (2006.01) | |
| *B01J 35/00* | (2006.01) | |
| *C08J 11/28* | (2006.01) | |
| *B01J 23/74* | (2006.01) | |
| *B01J 37/02* | (2006.01) | |

(52) U.S. Cl.
CPC ......... *C07C 67/333* (2013.01); *B01J 31/0284* (2013.01); *B01J 31/0292* (2013.01); *B01J 35/0033* (2013.01); *B01J 23/74* (2013.01); *B01J 37/0203* (2013.01); *B01J 37/0209* (2013.01); *C08J 11/28* (2013.01); *Y02W 30/706* (2015.05)

(58) Field of Classification Search
CPC . C07C 67/333; B01J 35/0033; B01J 31/0292; B01J 31/0284; B01J 37/0209; B01J 37/0203; B01J 23/74; C08J 11/28; Y02W 30/706

See application file for complete search history.

(56) References Cited

FOREIGN PATENT DOCUMENTS

| | | |
|---|---|---|
| CN | 101735061 A | 6/2010 |
| CN | 102020565 A | 4/2011 |
| CN | 102250868 A | 11/2011 |
| CN | 103100358 A | 5/2013 |
| NL | 2010439 | 3/2013 |
| WO | 2014209117 A1 | 12/2014 |

OTHER PUBLICATIONS

W (Wang et al, Fe-containing magnetic ionic liquid as an effective catalyst for the glycolysis of poly( ethylene terephthalate), Catalysis Communications 11 763-767 published 2010) (Year: 2010).*
Z (Zhang et al., Basic ionic liquids supported on hydroxyapatite-encapsulated-Fe2O3 nanocrystallites:An efficient magnetic and recyclable heterogeneous catalyst for aqueous Knoevenagel condensation, Journal of Molecular Catalysis A: Chemical 306 107-112 published 2009) (Year: 2009).*
International Search Report dated Sep. 10, 2014, for International Application No. PCT/NL2014/050418 filed Jun. 24, 2014 (5 pages).
International Preliminary Report on Patentability with Written Opinion for International Application No. PCT/NL2014/050418, dated Dec. 29, 2015 (7 pages).
Annex E6 to Appeal in European Patent Application No. 14753318.6 dated May 2016.
Appeal Brief in European Patent Application No. 14753318.6 dated Jun. 2, 2016.
Dalaigh, et al., "A Magnetic-Nanoparticle-Supported 4-N,N-Dialkylaminopyridine Catalyst: Excellent Reactivity Combined with Facile Catalyst Recovery and Recyclability", Angewandte Chemie International Edition, vol. 46, No. 23, 2007, 4329-4332.
M.H. Valkenberg, C. Decastro and W.F. Holderich, Immobilisation of ionic liquids on solid supports, 2002, Green Chemistry, The Royal Society of Chemistry, vol. 4, pp. 88-93.
M. Andriot, J.V, Degroot, Jr., et al., Silicones in Industrial Applications, chapter from book Inorganic Polymers, 2007, by R. De Jaeger and M. Gleria editors, Nova Science pu.
Ralph K. Iler, The Chemistry of Silica, Solubility, Polymerization, Colloid and Surface Properties, and Biochemistry, 1979, John Wiley & Sons Publishing, ISBN 0-471-02404-X.
Michael Freemantle, An Introduction to Ionic Liquids, Preface, Table of Contents, and Chapters 1, 3 and 8, year 2010, RSC Publishing, ISBN: 978-1-84755-161-0.
Sang-Gi Lee, Functionalized imiciazolium salts for task-specific ionic liquids and their applications, 2006, Chem. Commun., The Royal Society of Chemistry, pp. 1049-1063.
W (Wang et al, Fe-containing magnetic ionic liquid as an effective catalyst for the glycolysis of poly( ethylene terephthalate), Catalysis Communications 11 763-767 published (2010.
Z (Zhang et al., Basic ionic liquids supported on hydroxyapatite-encapsulated-Fe2O3 nanocrystallites: An efficient magnetic and recyclable heterogeneous catalyst for aqueous Knoevenagel condensation, Journal of Molecular Catalysis A: Chemical 306 107-112 published 2009.

(Continued)

*Primary Examiner* — Yevgeny Valenrod
*Assistant Examiner* — Blaine G Doletski
(74) *Attorney, Agent, or Firm* — Husch Blackwell LLP

(57) ABSTRACT

A method of degrading a polymer into oligomers and/or monomers in a solvent, using a catalyst, and a functionalized magnetic particle comprising a catalyst being capable of degrading the polymer into oligomers and/or monomers. The present method and particle provide a high selectivity and a high conversion ratio.

18 Claims, 2 Drawing Sheets

(56) References Cited

OTHER PUBLICATIONS

H (Hopewell et al., Plastics recycling: challenges and Opportunities, Phil. Trans. R. Soc. B 364, 2115-2126 published 2009). 061 (CN101735061 A 2010 translated).

Abu-Reziq, et al., "Metal Supported on Dendronized Magnetic Nanoparticles: Highly Selective Hydroformylation Catalysts", JACS, vol. 128, No. 15, 2006, 5279-5282.

Oliveira, et al., "Magnetic Fluids Based on γ-Fe2O3 and CoFe2O4 Nanoparticles Dispersed in Ionic Liquids", Journal of Physical Chemistry C, vol. 113, No. 20, 2009, 8566-8572.

Wang, et al., "Facile Preparation of Ionic Liquid Functionalized Magnetic Nano-Solid Acid Catalysts for Acetalization Reaction", Catalysis Letters, vol. 135, No. 1-2, 2010, 159-164.

Wang, et al., "Glycolysis of poly(ethylene terephthalate) catalyzed by ionic liquids", European Polymer Journal, vol. 45, No. 5, 2009, 1535-1544.

Zhang, et al., "A magnetic nanoparticle supported dual acidic ionic liquid: a "quasi-homogeneous" catalyst for the one-pot synthesis of benzoxanthenes", Green Chemistry, vol. 14, 2012, 201-208.

Zhang, et al., "Magnetic hydroxyapatite-encapsulated gamma-Fe2O3 nanoparticles functionalized with basic ionic liquids for aqueous Knoevenagel condensation", Applied Catalysis A: General, vol. 366, No. 1, 2009, 141-147.

Zhou, et al., "Effective Catalysis of Polyethylene terephthalate) (PET) degradation by metallic acetate ionic liquids", Pure and Applied Chemistry, vol. 84, No. 3, 2012, 789-801.

Dalaigh, et al., A Magnetic-Nanoparticle-Supported 4-N,N-Dialkylaminopyridine Catalyst: Excellent Reactivity Combined with Facile Catalyst Recovery and Recyclability, Angewandte Chemie, 2007, pp. 4407-4410, vol. 119.

* cited by examiner

POLYMER DEGRADATION

CROSS-REFERENCE TO RELATED APPLICATIONS

This application is a continuation of U.S. patent application Ser. No. 14/980,148 filed Dec. 28, 2015, which is a continuation of Patent Cooperation Treaty Application No. PCT/NL/2014/209117, entitled "POLYMER DEGRADATION", to Ioniqa B.V., filed on Jun. 24, 2014, which claims priority to Netherlands Patent Application No. 2011025, filed Jun. 24, 2013, and the specifications and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COM-PACT DISC

Not Applicable.

COPYRIGHTED MATERIAL

Not Applicable.

BACKGROUND OF THE INVENTION

Field of the Invention (Technical Field)

The present invention is in the field of a method of degrading a polymer into oligomers and/or monomers in a solvent, using a catalyst, and a functionalized magnetic particle comprising a catalyst being capable of degrading the polymer into oligomers and/or monomers. The present method and particle provide a high selectivity and a high conversion ratio.

DESCRIPTION OF RELATED ART

Various patent documents and scientific documents recite fluids comprising magnetic particles.

Magnetic Fluids are a class of smart materials that change their properties reversibly and relatively fast (milliseconds) under presence of an external magnetic field. These fluids can show changes in apparent viscosity of several orders of magnitude when a magnetic field is applied, such as a magnetic flux density in the order of around 1 T. Below two sub-classes are identified.

A ferrofluid relates to a liquid which becomes strongly magnetized in the presence of a magnetic field. Typically ferrofluids are colloidal liquids made of nanoscale ferromagnetic, or ferrimagnetic, particles suspended in a carrier fluid (usually an organic solvent or water). Typically each tiny particle is thoroughly coated with a surfactant to inhibit clumping. A disadvantage is that larger particles can be removed from an otherwise homogeneous colloidal mixture, forming a separate clump of magnetic dust e.g. when exposed to strong magnetic fields.

With respect to degradation of used polymers (or plastics) it is noted that in general this is hindered by lack of separation methods (e.g. separation of a first polymer from a second polymer, such as polyethylene (PE) and polypropylene (PP)). As a consequence a significant amount of used polymers is used as a fuel, which is burned.

It is noted that chemical recycling of polymers such as Polyethylene terephthalate (PET) is considered cost-efficient only applying relatively high capacity recycling lines of e.g. more than 50 ktons/year. Most likely such lines will only be combined with production sites of very large polymer producers. Several attempts of industrial magnitude to establish such chemical recycling plants have been made in the past but without resounding success. Even the promising chemical recycling in e.g. Japan has not become an industrial break through so far; there seem to be two main reasons therefore: first, a difficulty of consistent and continuous waste bottles sourcing in a required huge amount at one single site, and, at second, the steadily increased prices and price volatility of collected bottles. So despite huge amounts of PET produced on a yearly basis (>50.000 ktons) forming similar amounts of waste no economically feasible process has been introduced.

A further issue is that if a separation is (partly) successful, degradation into smaller building units still is difficult. Many methods or processes are not selective enough, that is a discrimination, shown by a reagent in competitive attack on two or more substrates or on two or more positions in the same substrate, is relatively low. It is typically quantitatively expressed by ratios of rate constants of the competing reactions, or by the decadic logarithms of such ratios. Further a conversion is too low; efficient conversion of reactants (polymers) to desired products (monomers or oligomers) without much wastage production in terms of side products is an issue. As a consequence a yield, being regarded as a product of selectivity times conversion, is too low as well.

A problem with a use of catalysts, especially catalysts in a solvent, is that it is virtually impossible to recover the catalyst after a first usage. As catalysts are typically quite expensive, one would like to recover a catalyst, at least largely, and reuse the catalyst a second time and preferably many more times. A small waste of catalyst would be acceptable, if a waste is in the order of a few percent or less. In this respect Wang (in Wang et al, "Fe-containing magnetic ionic liquid as an effective catalyst for glycolysis of poly (ethylene terephthalate)", Cat. Comm. 11 (2010), pp. 763-767, and in Eur. Pol. J., Pergamon Press Oxford, vol. 45, no. 5, 1 may 2009, pp. 1535-1544), and Xueyuan Zhou et al. (in Pure and Applied Chemistry, Vol. 84, No. 3, 1 Jan. 2012, pp. 789-801) mention degradation of PET using a catalyst, without reusing the catalyst and with moderate results. The amount of catalyst used in these processes is relatively high (17-80 wt %. catalyst per weight PET) and results are far from optimal.

Further it is in general considered a disadvantage to combine a catalyst to a support. Amongst others selectivity and conversion, as well as available catalyst are jeopardized. As such compared to non-combined catalyst typically more catalyst needs to be used in order to obtain similar results, and even then selectivity and conversion still worse. In this respect Valkenberg et al. in "Immobilisation of ionic liquids on solid supports", Green Chemistry, 2002 (4), pp. 88-93, shows ionic liquids attached to solid supports, e.g. a metal oxide, such as $TiO_2$, $SiO_2$, $Al_2O_3$, etc. Lee in "Functionalized imidazolium salts for task-specific ionic liquids and their applications", Chem. Commun., 2006, pp. 1049-1063 mentions similar catalysts. Such relate to a two-phase system. The results of the catalytic activity tested are considered rather poor, apart from some exceptions, especially in terms of conversion and selectivity. In other words the catalysts would not be considered to be used.

In general most catalysts are used for synthesis of molecules and the like, not for degradation. Typically catalysts, and especially catalyst complexes, and function of a catalyst are sensitive to contaminants being present; in other words they function only properly under relative pure and clean conditions. As a result of contamination catalysts need to be replaced regularly, and extreme care is typically taken not to introduce contaminants. That may also a reason why catalyst are typically not considered for degradation processes, as these processes almost inherently introduce contaminants.

In some instances metal catalysts are directly attached to a nanoparticle. Such catalysts are typically used for synthesis, but not for degradation, and certainly not for a reaction with at least one solid reactant. In this respect it is noted that for synthesis a reaction between two or more components is executed, wherein the two or more components are in close contact, such as in a solvent. The nature and relevant parameters of a synthesis reaction is considered to be quite different from degradation reactions; for instance relative low amounts of catalyst may be used and relatively high yield may be obtainable under optimal conditions. One can therefore not expect the teachings of synthesis reactions to be applicable to degradation reactions. Various articles, such as Zhang in Applied Catalysis A: General, Elsevier Science, Vol. 366, Nr. 1, pp. 141-147, Pang Wang in Catalysis Letters, Kluwer Academic Publishers-Plenum Publishers, NE, Vol. 135, Nr.-12, pp. 159-164, Raed Abu-Reziq in J. Am. Chem. Soc., ACS publications, Vol. 128, Nr. 15, pp. 5279-5282, Zhang in J. Mol. Cat. A: Chemical, Elsevier, Vol. 306, Nr. 1-2, pp. 107-112, 0 Dalaigh in Angewandte Chemie, Vol. 119, pp. 4407-4410, Oliveira in J. Phys. Chem. C, Vol. 113, Nr. 20, pp. 8566-8572 and Zhang in Green Chem., Vol. 14, pp. 201-208, relate to recoverable catalysts complex. However comparative data between catalyst per se and catalyst complex are absent. In other words, no improvement is shown and in fact a deterioration in respect of e.g. yield, amount used, efficiency, energy consumption, etc. is to be expected. Further some of the above catalyst complexes are not recovered magnetically, some relate to core-shell particles, some relate to conglomerates, Flavia does not show a complex, and some do not relate to an ionic liquid. Such is considered far from optimal.

The present invention provides a method and catalyst for degrading polymers which overcomes one or more of the above disadvantages, without jeopardizing functionality and advantages.

BRIEF SUMMARY OF THE INVENTION

The present invention relates in a first aspect to an improved reusable ionic catalyst complex for degradation of a homo or copolymer according to claim 1, and in a second aspect to a method according to claim 6, showing partly major improvements over the prior art, e.g. in terms of selectivity (93% versus 59.2%), conversion, yield, a very low amount of catalyst used per amount of product degraded/obtained (0.5-2 wt. % versus 17-80 wt. % [weight catalyst/weight polymer]), use of energy (1 hour versus 4 hours; so also much quicker), insensitivity to contaminants, insensitivity to composition of raw material to be degraded, etc. Put in numbers the present invention provides a conversion of about 100%, a selectivity of significantly more than 90% (versus some 59.2% prior art), reuse of catalyst (over 50 times, being absent in prior art degradation processes), allowing any mixture of waste polymers (not known in the prior art, typically well cleaned, well separated, having one type/source of material, is needed for prior art processes), a relatively modest temperature and pressure may be used (200° C. versus e.g. 500° C.), etc. It is noted that the present catalyst complex shows an improved localized action. It is also noted that typically improvement in one aspect (parameter) involves a deterioration in another aspect (parameter); the present range of improvements in various aspects together is already in that sense surprising.

The present catalyst complex comprises three distinguishable elements: a nanoparticle, a bridging moiety attached, such as by a covalent bond, to the nanoparticle and a catalyst entity (chemically) attached to the bridging moiety. The bridging moiety is solely in between the catalyst and the nanoparticle, respectively. The present complex is for instance different from a complex having a bridging moiety fully covering a nanoparticle, such as in a core-shell particle.

The present nanoparticle is of a magnetic nature. As such nanoparticles comprising a magnetic material are included, as well as particles that can be magnetized sufficiently under relative modest magnetic fields, such as being applied in the present method. It has been found that the nanoparticle should be sufficiently small for the catalyst complex to function as a catalyst, therewith degrading the present polymer into smaller units, wherein the yield of these smaller units, and specifically the monomers thereof, is high enough for commercial reasons. It is noted in this respect that a value of polymers to be degraded is relatively small, i.e. a costs of degrading should be small as well. It has also been found that the nanoparticle should be sufficiently large in order to be able to reuse the present complex by recovering the present catalyst complex. It is economically unfavorable to have catalyst complex being removed with either waste or degradation product obtained.

It is noted that the present nanoparticle is not considered to be a support. A prior art support in general relates to much larger entities, typically in the order of mm or larger. It is noted that for the present process a catalyst on a support is considered unsuited, in particular as a yield of degradation products is too low (or likewise time and/or temperature to obtain such a yield are unfavorable).

The present catalyst entity comprises at least two moieties. Such has been found to contribute to at least some of the present advantages. A first relates to an aromatic moiety having a positive charge. A second relates to a moiety, typically a salt complex, having a negative charge. The negative and positive charge typically balance one and another. It has been found that the positively and negatively charged moieties have a synergistic and enhancing effect on the degradation process of the polymer in terms of conversion and selectivity, especially in view of degrading polyesters and polyethers.

The aromatic moiety preferably comprises a heterocycle, having at least one, preferably at least two nitrogen atoms. The aromatic moiety preferably stabilizes a positive charge. The heterocycle may have 5 or 6 atoms, preferably 5 atoms.

The negatively charged moiety may relate to a salt complex, preferably a metal salt complex having a two- or three-plus charged metal ion, such as $Fe^{3+}$, $Al^{3+}$, $Ca^{2+}$, and $Cu^{2+}$, and negatively charged counter-ions, such as halogenides, e.g., $Cl^-$, $F^-$, $Br^-$.

The present catalyst entity and nanoparticle are combined by a bridging moiety. The person skilled in the art would expect that binding a catalyst entity, such as one according to the invention, onto a support would jeopardize the functioning of the catalyst entity, at least to some extent. Surprisingly, the present bridging molecule in combination with the nanoparticle provides a catalyst complex which functions almost as good as or better than the catalyst entity itself. It is noted that it is somewhat complicated to combine (or coat) the present nanoparticle with a bridging moiety, at least in terms of functionality obtained. It is not only important to provide suitable bridging moieties (or a combination thereof), but also to fit a number of bridging moieties with respect to a surface area of the present magnetic nanoparticle. In this respect also a size (diameter) of the present nanoparticle is important. For purpose of providing a catalyst complex suitable of degrading the present polymer the above needs to be taken into account; otherwise no effective degradation is obtained, e.g. in terms of conversion, selectivity, and economical feasibility. It is noted that up to now no economically viable process for polymer degradation has been provided.

In order to provide a suitable complex, having e.g. sufficient yield, selectivity, and conversion, it has been found that a proper functionalized magnetic particle is important. Inventors have established to produce a catalyst complex according to these requirements.

In an example of the present catalyst complex the magnetic particles have an average diameter of 2 nm-500 nm, preferably from 3 nm-100 nm, more preferably from 4 nm-50 nm, such as from 5-10 nm. As indicated above, the particles are preferably not too large and not too small. It has been found that e.g. in terms of yield and recovery of catalyst complex a rather small size of particles of 5-10 nm is optimal. It is noted that the term "size" relates to an average diameter of particles, wherein an actual diameter of a particle may vary somewhat due to characteristics thereof.

In an example of the present catalyst complex the bridging moiety is provided in an amount of (mole bridging moiety/gr magnetic particle) $5*10^{-6}$-0.1, preferably $1*10^{-5}$-0.01, more preferably $2*10^{-5}$-$10^{-3}$, such as $4*10^{-5}$-$10^{-4}$. It is preferred to have a relatively large amount available in terms of e.g. yield, energy consumption, etc., whereas in terms of amount of catalyst and costs thereof a somewhat smaller amount is available, especially as the magnetic nanoparticles are considered as a relatively cheap part of the catalyst complex. Surprisingly the present method can be performed with very low amounts of catalyst (complex), compared to prior art methods.

For the present method the solid polymer is provided in a suitable solvent. As such the present method may be considered as a solid-liquid degradation process supported by addition of a recoverable catalyst complex. For a glycolysis the solvent is preferably a mono- or di-alcohol. As such the solvent also functions as a reactant. Inventors have found that in view of recovery of the present catalyst complex not all solvents are suited. Some solvents form a stable "dispersion" with the catalyst complex; in such a case in the step of recovery a second solvent, e.g. functioning as washing agent, may be provided and the catalyst may then be recovered using an electromagnetic field.

The method may be carried out batch-wise, continuous, semi-continuous, and combinations thereof.

The present method has a less selective feedstock, as from virgin polymer (such as PET) to various other recovered sources may be provided. Also it provides a relatively low energy process. As a consequence polymer produced from the present degradation products is considered to be 'Green' produced, such as in a case of PET up to 25%.

The present method can be considered to relate to a one-phase system for degradation, comprising a solvent, a polymer to be degraded, and a catalyst complex. Such a system may also be referred to as a dispersion in that particles (polymer and catalyst complex) are present in a solvent. It is noted that in general it is difficult to obtain a (time) stable one-phase system. In this respect the present method distinguishes itself from a reaction with a catalyst on a support, which effectively relates to a two-phase system, not being suitable for polymer degradation.

The temperature and pressure of the method may be adjusted. Typically a somewhat higher temperature is preferred in terms of reaction velocity; a lower temperature is preferred in terms of energy consumption. Likewise a higher pressure is somewhat preferred; in view of complexity of an installation a lower pressure is preferred, that is a pressure being about 100 kPa. It is an advantage of the present method that a relatively low temperature may be used, without jeopardizing yield. It is also an advantage that using relatively mild temperature and pressure conditions the present degradation can be carried out in a relative short time. Such provides e.g. a relative high throughput, a relatively smaller installation, and lower consumption of materials and energy.

It is a further advantage of the present method that the method is relatively insensitive (e.g. in terms of yield) for mixed polymers being provided. Mixed polymers can relate to a combination of two or more different types of polymers, such as different polyesters, such as PET, polyethylene furanoate (PEF), and polybutylene terephthalate (PBT), to a combination of one type of polymer having different properties, such as color, thickness, origin, and combinations thereof. Also the method is relatively insensitive to contaminants, like additives, such as pigments, fillers, filters, etc. As such the present method is considered robust, to be used under relatively sub-optimal conditions, such as in a plant.

Compared to prior art method a characteristic of the present method is that the catalyst complex is recovered. It is preferred to use the present catalyst complex in the present method.

Thereby the present invention provides a solution to one or more of the above mentioned problems. The various examples and embodiments of the present invention may be combined.

Advantages of the present description are detailed throughout the description.

DETAILED DESCRIPTION OF THE INVENTION

The present invention relates in a first aspect to a catalyst complex according to claim 1.

In an example of the present catalyst complex the magnetic particles are one or more of ferromagnetic particles, antiferromagnetic particles, ferrimagnetic particles, synthetic magnetic particles, paramagnetic particles, superparamagnetic particles, such as particles comprising one or more of Fe, Co, Ni, Gd, Dy, Mn, Nd, Sm, and preferably one or more of O, B, C, N, such as iron oxide, such as ferrite, such as magnetite, hematite, and maghemite. In view of degradation yield magnetite and maghemite are preferred magnetic particles. In view of costs, even when fully or largely recovering the present catalyst complex, relatively cheap particles are preferred, such as particles comprising Fe. It is noted that it is not possible to just choose a magnetic metal and/or counter-ion at random; present inventors have found that some sophisticated tailoring is required.

In an example of the present catalyst complex the bridging moiety is one or more of a weak organic acid, silanol, silyl comprising groups, such as silylethers, such as triethoxysilylpropyl, and silanol. It has been found that despite negative expectations these bridging groups do not result in a non-acceptable reduced performance of the catalyst entity.

In an example of the present catalyst complex the aromatic moiety has at least one tail, the at least one tail preferably having a length of $C_1$-$C_6$, such as $C_2$-$C_4$, the at least one tail being attached to the at least one nitrogen atom. It has been found that for an optimal degradation a somewhat higher yield is obtained when the present tail is somewhat longer. In terms of mass of catalyst complex provided it has been found that a somewhat shorter tail is preferred.

In an example of the present catalyst complex the magnetic nanoparticle comprises (per particle) at least one bridging moiety and catalyst entity, preferably 2-$10^4$ bridging moieties and catalyst entities, more preferably 10-$10^3$ bridging moieties and catalyst entities. In principle, e.g. in view of yield, as many catalyst entities as possible may be provided. However the amount of catalyst entities and there functioning is in view of e.g. degradation efficiency somewhat smaller than an amount that could be achieved. Also when a larger particle is selected somewhat more catalyst entities may be present.

In an example of the present catalyst complex the amount of bridging moiety and catalyst attached thereto is 0.03-99 wt. %, preferably 0.1-75 wt. %, more preferably 0.2-25 wt. %, even more preferably 0.3-10 wt. %, relative to a total weight of catalyst complex. Likewise as above, a relative low amount of 0.5-5 wt. % of catalyst entity has been found to be optimal, such as 0.6-3 wt. %, within further boundary conditions such as applied temperature. It is noted that the present catalyst and bridging moiety may form a single (mono-) layer, a double (bi-) layer, a oligo-layer, and combinations thereof. Before applying the present catalyst complex in the present method it may be washed. The above weight percentages are relative to a total weight of catalyst complex.

In a second aspect the present invention relates to a method according to claim 6. Therein a polymer is provided in solid form. Preferably the polymer is fragmented into smaller pieces.

In an example of the present method the polymer is a mixture of waste polymers, the mixture optionally comprising one or more of coloured polymers. The present method is capable of handling waste polymers, and even further a mixture of polymers, e.g. having different characteristics, such as a different colour. The yield of degradation has been found not to be influenced noticeably. It is noted that prior art methods at the most can only handle relatively pure waste polymer, and even then results are discouraging.

In an example of the present method the constituents such as solvent, catalyst complex and polymer, form a one-phase system. Such has been found advantageous, especially in terms of yield obtained. Also in terms of reactor design such is advantageous.

In an example of the present method the polymer may selected from natural polymers, biobased polymers, biodegradable polymers, polymers formed (directly or indirectly) from fossil fuels, and combinations thereof. In an example the polymer is one or more of a polyester, a polyether, such as polyoxymethylene (POM), polyethyleneglycol (PEG), polypropyleneglycol (PPG), polytetramethyleneglycol (PTMG), polyethyleneoxide (POE), polypropyleneoxide (PPO), polytetrahydrofuran (PTHF), and polytetramethyleneetherglycol (PTMEG), a polyalkene, a polyalkane, a polypeptide, a polyamide, a polyamine, a polycondensate, preferably a polyester, such as poly carboxylic ester, wherein the poly carboxylic ester is preferably selected from polyethylene terephthalate (PET), polyethylene furanoate (PEF), polybutylene terephthalate (PBT), polytrimethylene terephthalate (PTT), polyglycolic acid (PGA), polylactic acid (PLA), polycaprolactone (PCL), polyethylene adipate (PEA), polyhydroxyalkanoate (PHA), polyhydroxybutyrate (PHB), polyethylene naphthalate (PEN), Poly(3-hydroxybutyrate-co-3-hydroxyvalerate) (PHBV), and a polycondensate of 4-hydroxybenzoic acid and 6-hydroxynaphthalene-2-carboxylic acid (VECTRAN). In other words a large variety of polymers may be degraded by the present method. Some adjustments may be necessary, e.g. in terms of catalyst used, temperature applied, solvent used, etc. The present method is best suited for degradation of polyesters and polyethers.

In an example of the present method the solvent is a reactant, the reactant being capable of reacting with the polymer being degraded, and preferably forming a mono- or di-ester with the monomer, such as an alkanol and alkanediol, preferably methanediol, ethanediol, and propanediol, water, and amino comprising reactants. In terms of e.g. reactor design and complexity of reaction such is an advantage. Further, a product obtained can e.g. in case of degradation of PET be directly used as feed-stock for PET production.

In an example of the present method wherein the degrading is performed during a period of 0.1 minutes-168 hours, preferably 1 minutes-48 hours, more preferably 5 minutes-24 hours, even more preferably 15 minutes-12 hours, such as 1 hours-3 hours. The shorter periods possible are considered relative short, especially as compared to prior art processes. Depending on e.g. reactor size and boundary conditions longer or shorter periods may be used. For instance, a high pressure (500-3000 kPa) process at a temperature of 150° C.-350° C. leads to very short degrading times, in the order of minutes. Such indicates that the present method, and catalyst complex used therein, provide a large amount of design freedom.

In an example of the present method the degrading is performed at a temperature of 50° C.-500° C., preferably 90° C.-350° C., more preferably 150° C.-250° C., even more preferably 170° C.-200° C., such as 180° C.-190° C. The preferred range is considered to relate to a relative mild temperature, especially as compared to prior art processes which are performed at temperatures above 300° C. Even further, as the temperature applied is relatively mild, waste energy of an adjacent plant may be used for the present process. It is noted that the present catalyst complex has been found to be stable (enough) under the conditions mentioned, such as the above temperature. The present complex does not volatilize under the present conditions.

In an example of the present method the amount of catalyst is 0.1-35 wt. %, preferably 0.5-20 wt. %, more preferably 1-10 wt. %, even more preferably 2-5 wt. %, relative to a total weight of polymer provided. If the amount of catalyst is higher a shorter reaction time was obtained, whereas at a lower amount longer reaction times were obtained. Depending on further boundary conditions one may vary the amount of catalyst. Here the amount of catalyst relates to the catalyst entity and bridging moiety, i.e. without nanoparticle.

In an example of the present method the pressure is from 90 kPa-10.000 kPa, preferably 100 kPa-8.000 kPa, more preferably 200 kPa-2.000 kPa. Mild pressures in an example are an advantage over some prior art processes, which need to be performed at relatively high pressures, of e.g. 1000 kPa, often in combination with a high temperature.

In a selection of a combination of temperature and pressure a range of [T,P] from [180° C., 60 kPa] to [450° C., 8.200 kPa] may be chosen, preferably from [250° C., 420 kPa] to [400° C., 4.960 kPa], such as from [280° C., 790 kPa] to [350° C., 2.560 kPa]. For the combinations the degradation time is found to be from 1.5 hours @[180° C., 60 kPa] to about 20 seconds @[450° C., 8.250 kPa]. For safety reasons the degradation is best carried out at a temperature below 350° C. and below a pressure of 6.000 kPa, depending on the solvent.

In an example of the present method the polymer is provided as small particles, such as pellets, particles, and granules, having a volume of less than 100 cm$^3$, preferably $1*10^{-6}$ mm$^3$-64 cm$^3$, more preferably 0.001 mm$^3$-27 cm$^3$, even more preferably 0.01 mm$^3$-8 cm$^3$, such as 0.03 mm$^3$-1 cm$^3$. Such may require an extra process step of reducing a size of polymer provided, e.g. shredding PET-bottles and grinding. It may be somewhat costly to pelletize or granulize polymer; in view thereof somewhat larger pellets or granules are preferred. In view of e.g. yield and size of a plant smaller pellets or granules are preferred. However, in view of environmental and health issued pellets or granules are preferably not too small. A size of 0.03 mm$^3$-1 cm$^3$ has been found to be optimal, especially for PET. It is noted that also polymer bottles as such may be provided, possibly shredded to some extent.

In an example of the present method further comprises the step of recovering the catalyst attached to the magnetic particle using an electro-magnetic field gradient, preferably in a magnetic field of 0.1-5 T, preferably from 0.3-2 T, more preferably from 0.5-1.5 T, such as 0.8-1.3 T, e.g. 1 T. As such a relatively small magnetic field is found to be sufficient to recover the present catalyst complex. In view of e.g. reactor design such is advantageous. In an example water is provided, in order to separate the present complex from the present solvent. It has been found that it is much easier to remove the present complex from a water phase, than from the present solvent phase. By providing a suited catalyst complex, such as the present complex, the catalyst (complex) may be recovered. It has been found that typically 95% of the catalyst complex can be recovered, and often even 98-99%. As a consequence the present catalyst complex can be reused 20-100 times, thereby e.g. saving costs. It has been found that a recovered catalyst complex functions equally well compared to a fresh (non-used) complex.

In an example of the present method further comprises the step of recycling the catalyst complex. After recovery the present complex can be recycled to the present degradation process, or removed and e.g. stored for later use.

In an example of the present method further comprises the step of removing additives from the solvent, the additives being added to the polymer when these where produced. The additives may for instance be removed after adding water and applying a magnetic field; in that case additives are effectively separated from a phase wherein further the present catalyst, oligomers, trimers and dimers may be present. Such is advantages as in principle these additives are at this stage not reused, whereas the degradation products are reused, possibly formed into novel polymer.

In an example of the present method further comprises the step of retrieving trimers, dimers, and/or monomers, preferably free of additives and contaminants, such as by chemical and/or physical separation, in one step, or in a combination of steps. In a first step of retrieving e.g. water may be added. Monomers and solvent may dissolve in water, whereas catalyst complex, additives, oligomers, trimers and dimers, especially under influence of an external magnetic field, will form a separate phase. The catalyst complex, additives, oligomers, trimers and dimers may be reintroduced in a first reaction step, wherein the polymer is degraded. In a second step of retrieving the monomers can be retrieved by providing e.g. water, and then "crystallizing". As such the degradation products are ready to be reused, in fact without a further need to e.g. purify these products.

In an example of the present method the polymer is polyethylene terephthalate (PET) or PEF, the solvent is ethanediol, the catalyst comprises butylmethylimidazolium (bmim$^+$) and FeCl$_4^-$, the bridging moiety is triethoxysilylpropyl, and the nanoparticle is magnetite and/or maghemite. The nanoparticles preferably have a size of 5-10 nm. The bridging moiety preferably is present in an amount of $10^{-4}$-$10^{-2}$ mole bridging moiety/gr nanoparticle, such as $2*10^{-4}$-10. Such is especially a preferred embodiment in view of the abundant amount of waste PET being available, being in excess of hundreds of thousand tons per year.

In an example of the present method further comprises the step of adjusting an amount of partly negative charged molecules, such as by adding a salt, preferably a Fe$^{3+}$ comprising salt, such as an halogenide, such as by adding FeCl$_3$. Surprisingly the yield of the present method and the functioning of the catalyst complex can be maintained at a high level by adjusting an amount of the partly negatively charged molecules used. Such is step is relatively simple to carry out, and costs thereof are considered minimal.

In an example of the present method further comprises the step of providing oligomers to the solvent, preferably oligomers produced by the method. As such the oligomers may be degraded further, into dimers and monomers, in a subsequent step. The subsequent step may be carried out in the same place as an initial step, e.g. in the same reactor.

The invention is further detailed by the accompanying figures and examples, which are exemplary and explanatory of nature and are not limiting the scope of the invention. To the person skilled in the art it may be clear that many variants, being obvious or not, may be conceivable falling within the scope of protection, defined by the present claims.

DETAILED DESCRIPTION OF FIGURES

Figure 1A:
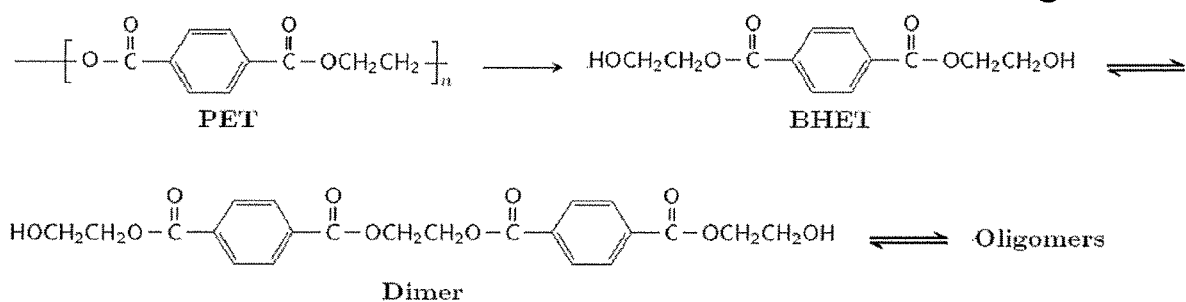
FIG. 1a-c shows chemical reactions and catalyst complexes.

FIG. 1a shows chemical reactions. Therein poly(ethylene terephthalate) is degraded by using (bmim) FeCl$_4$ in 1,2-ethanediol. As a result Terephthalic Acid Bis(2-Hydroxyethyl) ester (BHET) is formed. Further, it is shown that BHET can be converted into dimers and oligomers.

Figure 1B:
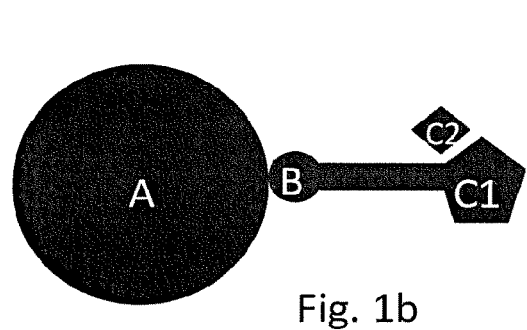

FIG. 1b shows a schematic representation of the present catalyst complex. Therein A represents a nanoparticle, B a bridging moiety, and C a catalyst entity with C1 being a positive catalyst moiety and C2 being a negative catalyst moiety.

Figure 1C:
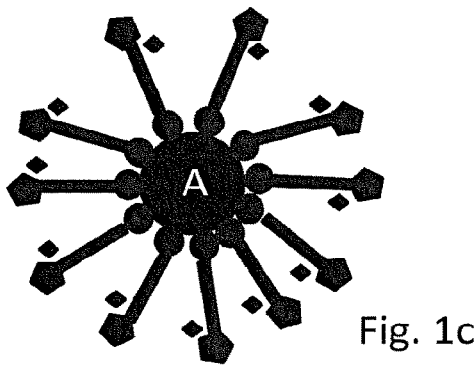

FIG. 1c shows a nanoparticle A surrounded by a number of bridging moieties and catalyst entities.

Figure 2:
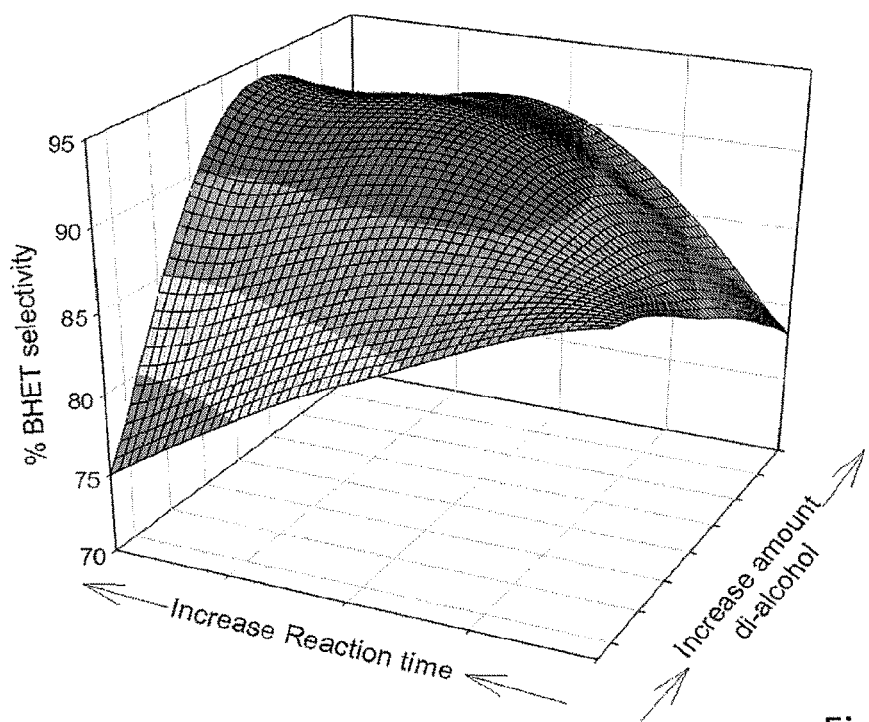
FIG. 2 shows selectivity percentages of BHET.

FIG. 2 shows selectivity percentages of BHET (vertical axis), obtained from depolymerization of colored PET, as function of reaction time and amount of di-alcohol (1,2-ethanediol) (horizontal axes). The PET provided was cut into pieces of about 2×2 cm$^2$. In another example pieces of about 0.3×0.3 cm$^2$, and in a further example as small particles having an average diameter of 50 μm. The size of the pieces was found to be not particularly relevant for the outcome. A reaction temperature was about 197° C. Results were obtained by varying a reaction time and amount of di-alcohol. For all degradation reactions performed, the corresponding PET conversion rates obtained are close to 100% (typically 99-99.99%, as no PET-pieces could be observed anymore in the solvent), which are considered to be very high. The selectivity rates (>90%, in a best case scenario so far >93%) are considered to be very high as well. The yield is as a result also >90%, and up to 93%. Even further the rates are obtained in a relatively short time frame. The selectivities are obtained with 2 wt. % catalyst (including bridging moiety and catalyst) relative to a total amount of polymer, respectively. So a small amount of catalyst is already sufficient.

So despite negative expectations that use of a catalyst complex would reduce selectivity, conversion and yield, the present method (and catalyst complex used therein) provides much better results e.g. in these respects than prior art methods (using a catalyst per se). Losses are already reduced from about 20-40% (prior art) to less than 7%.

EXAMPLES

Similar tests as above haven been performed on non-colored PET. The results thereof are in the same order of magnitude for both conversion and selectivity. As a consequence inventors conclude that a color additive has hardly any or no impact in this respect. Even further, additives, such as pigments, can be removed from the degradation products, with ease.

Similar tests as above have been performed on a wide range of raw (PET) material, e.g. polyester clothing, PET carpet, PET material from automotive industry, recycled PET, multi-layered PET trays containing other polymers, such as PE and PP. The results thereof are in the same order of magnitude for both conversion and selectivity, and thus for yield. As a consequence inventors conclude that the process is highly insensitive to different raw (PET) material and robust as well.

Similar tests were performed on amorphous (AMP) pellets and solid state polymerization (SSP) pellets. Again PET conversion and BHET selectivity were high. Values obtained for SSP pellets were somewhat lower, relatively. It is considered that possibly due to a somewhat longer chain length of the polymer to be degraded selectivity and conversion are somewhat jeopardized.

The invention although described in detailed explanatory context may be best understood in conjunction with the accompanying examples and figures. It should be appreciated that for commercial application it may be preferable to use one or more variations of the present system, which would similar be to the ones disclosed in the present application and are within the spirit of the invention.

What is claimed is:

1. Method of degrading a homo- or copolymer into oligomers, trimers, dimers and/or monomers, comprising the steps of:
providing the polymer in a suitable solvent, the polymer being in solid form, wherein the polymer is one or more of a polyester, a polyamide, a polycondensate and a polyether, wherein the solvent is a mono- or di-alcohol, providing a catalyst complex being capable of degrading the polymer into oligomers and/or monomers, wherein the polymer, solvent and catalyst complex constitute a dispersion, wherein said catalyst complex comprising functionalized magnetic particles, wherein the functionalization comprises a bridging moiety and a catalyst entity bonded to the bridging moiety, said catalyst entity comprising an aromatic heterocyclic moiety,
degrading the polymer by means of glycolysis to degrade a portion thereof into oligomers, trimers, dimers and monomers, in which the solvent functions as a reactant, and wherein the degradation is performed at a temperature in the range of 90°-350° C. and a pressure in the range of 90 kPa-6,000 kPa,
recovering the catalyst complex, wherein a second solvent is provided as a washing agent, said second solvent being water, wherein the catalyst complex, oligomers trimers and dimers form a separate phase, and wherein monomers and the mono- or di-alcoholic solvent dissolve in the water, and
retrieving monomers from the second solvent by means of crystallisation.

2. Method according to claim 1, wherein the polymer is a mixture of waste polymers.

3. The method as claimed in claim 2, wherein the said mixture comprises one or more of coloured polymers comprising color additives.

4. Method as claimed in claim 3, wherein said color additives go into the separate phase upon addition of the second solvent.

5. Method as claimed in claim 3, wherein the color additives comprise pigment.

6. Method according to claim 1, wherein the polymer is a polyester.

7. Method as claimed in claim 6, wherein the polyester is a poly carboxylic ester.

8. Method as claimed in claim 7, wherein the poly carboxylic ester is selected from polyethylene terephthalate (PET), polyethylene furanoate (PEF), polybutylene terephthalate (PBT), polytri-methylene terephthalate (PTT), polyglycolic acid (PGA), polylactic acid (PLA), polycaprolactone (PCL), polyethylene adipate (PEA), polyhydroxyalkanoate (PHA), polyhydroxybutyrate (PHB), polyethylene naphthalate (PEN), Poly (3-hydroxybutyrate-co-3-hydroxyvalerate) (PHBV), and a polycondensate of 4-hydroxybenzoic acid and 6-hydroxynaphthalene-2-carboxylic acid (VECTRAN).

9. Method as claimed in claim 1, further comprising the step of providing oligomers obtained by degradation of the polymer to the solvent.

10. Method as claimed in claim 9, wherein the provision of catalyst complex comprising introducing a mixture of catalyst complex, oligomers, trimers, dimers and additives if any, which mixture is obtained in a preceding degradation process in the recovery step.

11. Method as claimed in claim 1, wherein the reaction conditions of degrading the homo- or copolymer is in the range of 170° C.-200° C.

12. Method as claimed in claim 1, wherein degradation of the polymer is carried out such that at least 99% of the polymer is degraded into oligomers, trimers, dimers and monomers.

13. Method as claimed in claim 1, wherein the solvent is a di-alcohol.

14. Method according to claim 1, wherein the degrading is performed during a period of 15 minutes-3 hours.

15. Method as claimed in claim 1, wherein the amount of catalyst is 0.1-10 wt. %, relative to a total weight of polymer provided.

16. Method according to claim 1, wherein the polymer is provided as particles, pellets or granules, having a volume of 0.01 mm³-8 cm³.

17. Method as claimed in claim 15, wherein the volume is 0.03 mm³-1 cm³ per particle, pellet or granule.

18. Method according to claim 1, wherein the polymer is polyethylene terephthalate (PET) or polyethylene furanoate (PEF), the solvent is ethanediol, the catalyst entity comprises imidazolium, the bridging moiety is triethoxysilylpropyl, and the nanoparticle is one or more of magnetite, hematite, and maghemite.

* * * * *